(12) United States Patent
Dale et al.

(10) Patent No.: US 10,064,405 B2
(45) Date of Patent: *Sep. 4, 2018

(54) SIMULATED ENVIRONMENT FOR TRANSCATHETER HEART VALVE REPAIR

(71) Applicant: St. Jude Medical, Cardiology Division, Inc., St. Paul, MN (US)

(72) Inventors: Theodore Paul Dale, Corcoran, MN (US); Aaron J. Chalekian, Savage, MN (US); James Leo Kurk, New Richmond, WI (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/365,093

(22) Filed: Nov. 30, 2016

(65) Prior Publication Data
US 2017/0079263 A1 Mar. 23, 2017

Related U.S. Application Data

(63) Continuation of application No. 14/195,231, filed on Mar. 3, 2014, now Pat. No. 9,539,094.

(60) Provisional application No. 61/780,052, filed on Mar. 13, 2013.

(51) Int. Cl.
| | |
|---|---|
| *G09B 23/28* | (2006.01) |
| *A01N 1/02* | (2006.01) |
| *A61B 17/00* | (2006.01) |
| *A61B 17/064* | (2006.01) |

(Continued)

(52) U.S. Cl.
CPC .......... *A01N 1/0247* (2013.01); *A01N 1/021* (2013.01); *A61B 17/00234* (2013.01); *A61B 17/0644* (2013.01); *A61F 2/2472* (2013.01); *G01N 1/36* (2013.01); *A61B 2017/00243* (2013.01); *A61B 2017/00349* (2013.01); *A61B 2017/0645* (2013.01); *A61F 2/2457* (2013.01); *A61F 2/2463* (2013.01); *A61F 2/2466* (2013.01); *A61F 2220/0008* (2013.01)

(58) Field of Classification Search
USPC ............... 434/262, 267, 268, 272, 295, 296
See application file for complete search history.

(56) References Cited

U.S. PATENT DOCUMENTS

| | | |
|---|---|---|
| 5,425,644 A | 6/1995 | Szinicz |
| 5,634,797 A | 6/1997 | Montgomery |
| 5,947,744 A | 9/1999 | Izzat |

(Continued)

*Primary Examiner* — Kurt Fernstrom
(74) *Attorney, Agent, or Firm* — Lerner, David, Littenberg, Krumholz & Mentlik, LLP

(57) ABSTRACT

An apparatus for applying liquid pressure to resected tissue may include a fixture, a papillary assembly coupled to the fixture and having first and second spaced apart papillary attachment elements, and a resected mitral valve attached to the fixture. The fixture may have a first chamber, a second chamber, and an internal panel extending between the first and second chambers. The resected mitral valve may be attached to the internal panel and may have a posterior leaflet, an anterior leaflet, and tendinae chordae. The tendinae chordae may each be attached at a first end to the posterior leaflet or the anterior leaflet and at a second end to one of the papillary attachment elements. A first group of the tendinae chordae may be attached to the first papillary attachment element, and a second group of the tendinae chordae may be attached to the second papillary attachment element.

20 Claims, 14 Drawing Sheets

(51) Int. Cl.
*G01N 1/36* (2006.01)
*A61F 2/24* (2006.01)

(56) References Cited

U.S. PATENT DOCUMENTS

| | | |
|---|---|---|
| 6,790,043 B2 | 9/2004 | Aboud |
| 7,018,327 B1 | 3/2006 | Conti |
| 7,083,418 B2 | 8/2006 | Baldauf |
| 8,678,830 B2 | 3/2014 | Gurdin et al. |
| 8,926,333 B2 | 1/2015 | Vozenilek et al. |
| 9,183,763 B2 | 11/2015 | Carson et al. |
| 2007/0254273 A1 | 11/2007 | LaFrance et al. |
| 2009/0246747 A1 | 10/2009 | Buckman, Jr. |
| 2015/0161347 A1 | 6/2015 | Christiansen et al. |

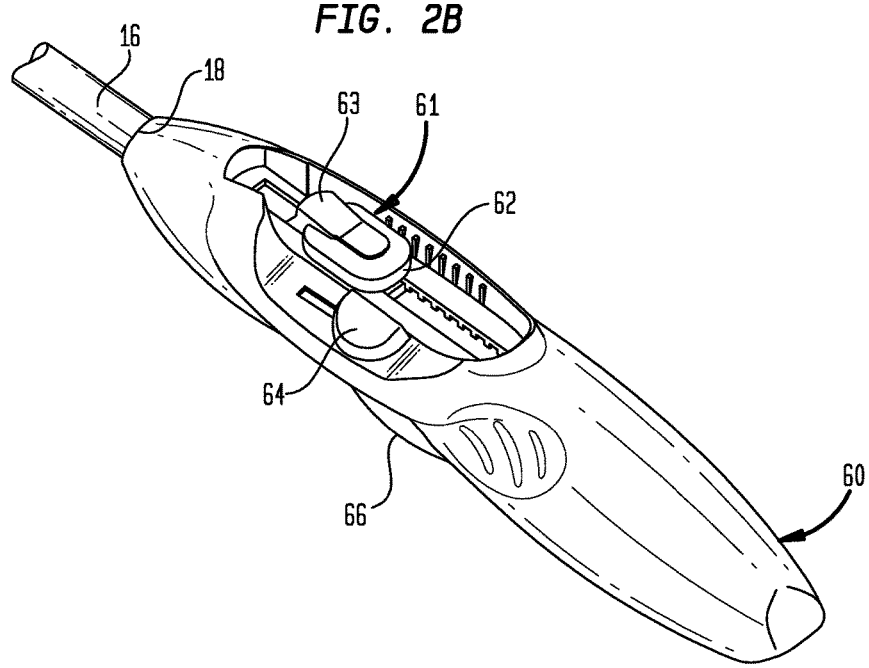
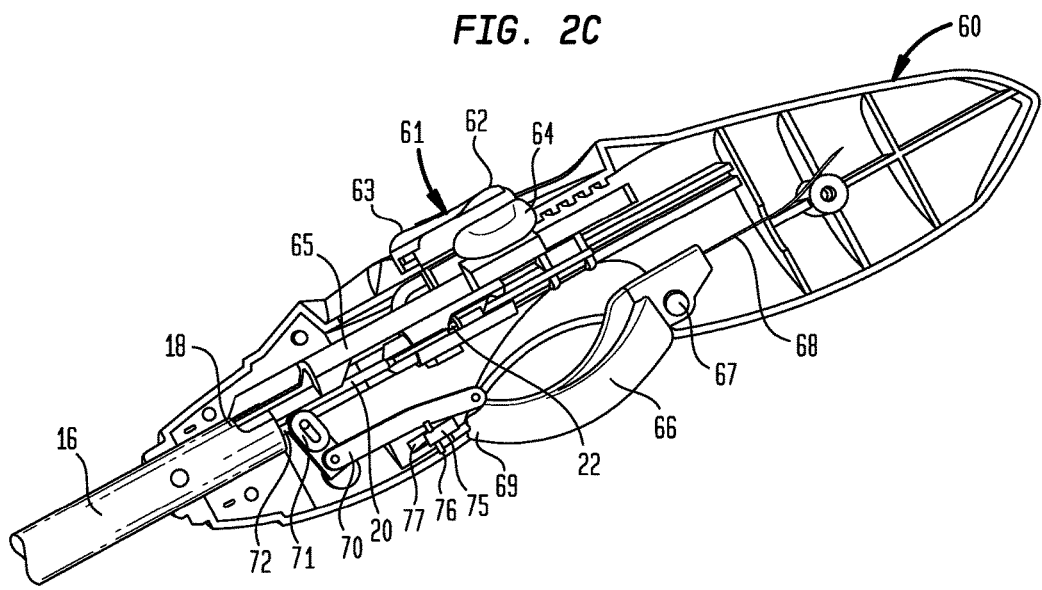

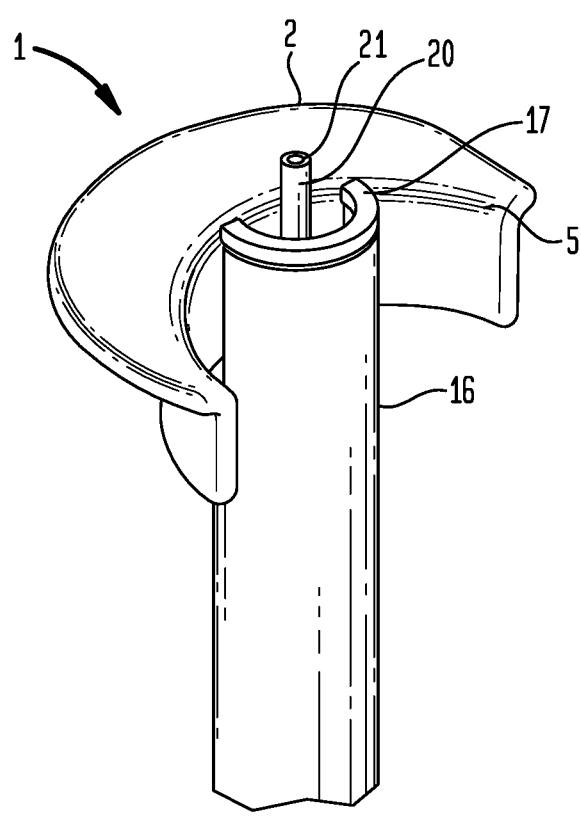

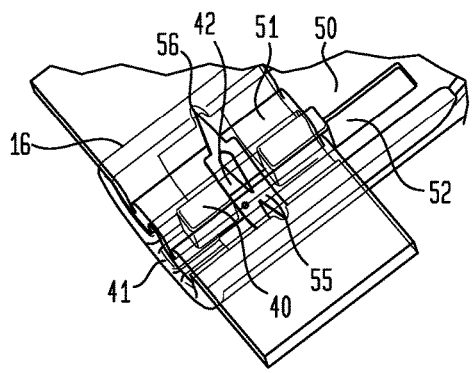
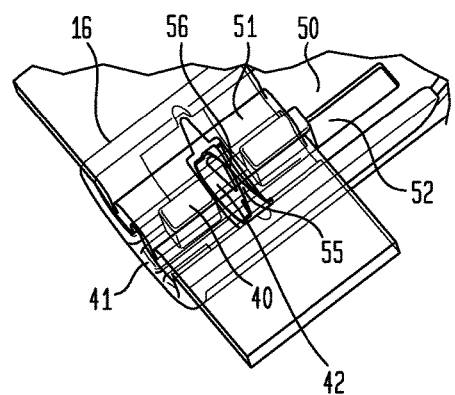
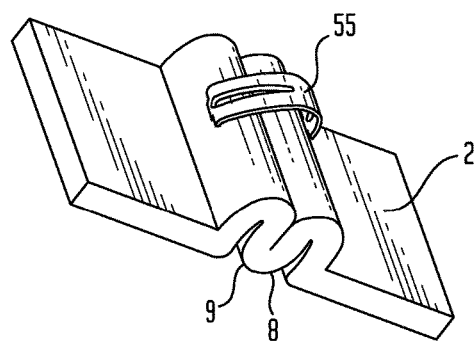
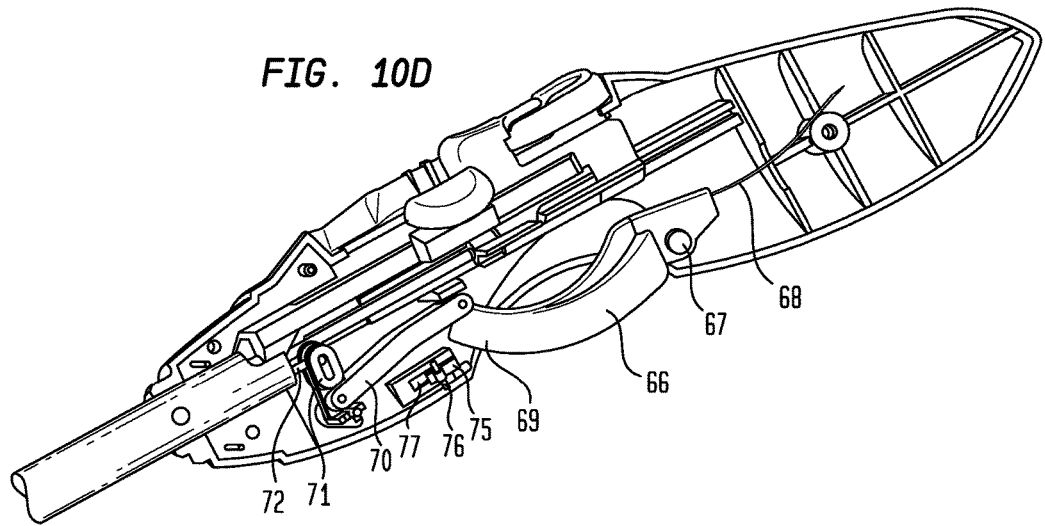

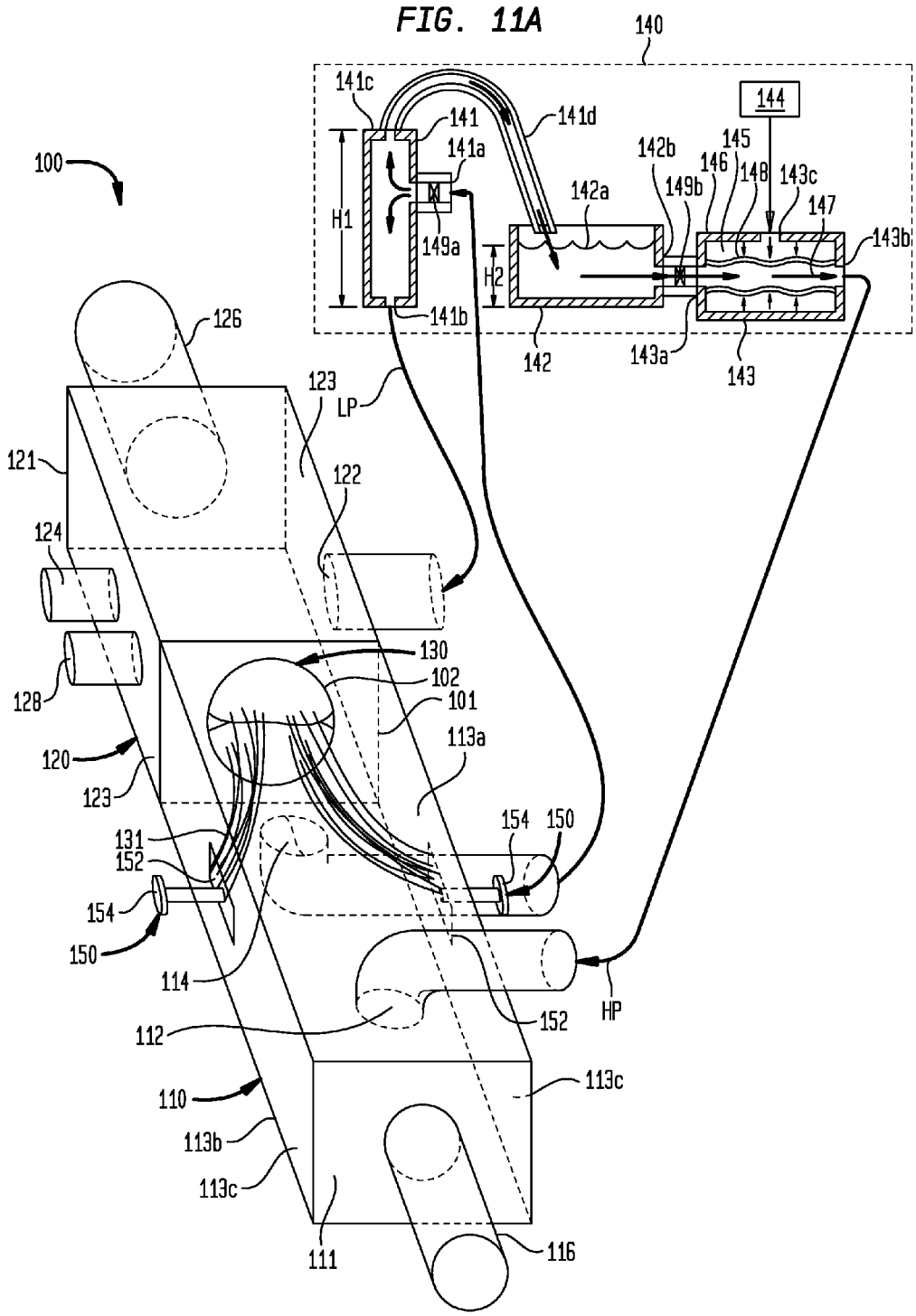

SIMULATED ENVIRONMENT FOR TRANSCATHETER HEART VALVE REPAIR

CROSS-REFERENCE TO RELATED APPLICATION

The present application is a continuation of U.S. patent application Ser. No. 14/195,231, filed Mar. 3, 2014, which claims the benefit of the filing date of U.S. Provisional Patent Application No. 61/780,052 filed Mar. 13, 2013, the disclosures of which are hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be broken. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

Devices and methods of mitral valve leaflet repair may be tested in simulated environments (e.g., in large animals or in testing equipment) before the devices and methods are used in human patients. Typically, mitral valve leaflet repair devices and methods are tested in environments that may not be accurately representative of the structure, function, and attachment of a loose or floppy posterior leaflet, which may result in inaccuracies in the simulated leaflet repair compared to how such a repair would be accomplished inside of a live patient.

There therefore is a need for improvements to the devices, systems, and methods for simulated repair of mitral valve leaflets. Among other advantages, the present invention may address one or more of these needs.

BRIEF SUMMARY OF THE INVENTION

A simulated environment for transcatheter repair of heart valve leaflet tissue and methods of simulating an environment for transcatheter repair of heart valve leaflet tissue using same are aspects of the invention. In addition, any device having one or more of the following features and used in the transcatheter repair of heart valve leaflet tissue are the specific aspects of the invention.

An apparatus for applying liquid pressure to resected tissue may include a fixture, a papillary assembly coupled to the fixture and having first and second spaced apart papillary attachment elements, and a resected mitral valve attached to the fixture. The fixture may have a first chamber, a second chamber, and an internal panel extending between the first and second chambers. The fixture may have at least one introducer configured to receive an elongated catheter assembly therethrough. Each papillary attachment element may be movable relative to the internal panel in at least one degree of freedom. The resected mitral valve may be attached to the internal panel and may have a posterior leaflet, an anterior leaflet, and tendinae chordae. The tendinae chordae may each be attached at a first end to the posterior leaflet or the anterior leaflet and at a second end to one of the papillary attachment elements. A first group of the tendinae chordae may be attached to the first papillary attachment element, and a second group of the tendinae chordae may be attached to the second papillary attachment element.

Each papillary attachment element may be movable relative to the internal panel in six degrees of freedom. Each papillary attachment element may include a suture plate. The tendinae chordae may each be attached to the papillary attachment elements through a resected portion of a papillary muscle. The fixture may further include first and second side panels disposed at opposite sides of the internal panel. The first and second papillary attachment elements may each have a control rod extending through the respective first and second side panels. The papillary attachment elements may each be at least partially disposed inside the first chamber, and a portion of the introducer may be in fluid communication with the first chamber. The papillary attachment elements may each be at least partially disposed inside the first chamber, and a portion of the introducer may be in fluid communication with the second chamber.

The apparatus may also include a pumping system configured to provide liquid flow through the resected mitral valve. The papillary attachment elements may each be at least partially disposed inside the first chamber, and the pumping system may be configured to alternatingly provide high pressure liquid flow into the first chamber and low pressure liquid flow into the second chamber. The fixture may include an outlet port in fluid communication with the first chamber and the pumping system. The outlet port may include an artificial aortic valve.

Another apparatus for applying liquid pressure to resected tissue may include a fixture and a papillary assembly coupled to the fixture and having first and second spaced apart papillary attachment element. The fixture may have a first chamber, a second chamber, and an internal panel extending between the first and second chambers. The fixture may have at least one introducer configured to receive an elongated catheter assembly therethrough. The internal panel may have an opening extending therethrough between the first and second chambers. The internal panel may be configured to receive a resected mitral valve attached thereto and in fluid communication with the opening. Each papillary attachment element may be movable relative to the internal panel in at least one degree of freedom. Each papillary attachment element may be configured to have tendinae chordae of the resected mitral valve attached thereto.

Each papillary attachment element may be movable relative to the internal panel in six degrees of freedom. Each papillary attachment element may include a suture plate configured to have the tendinae chordae of the resected mitral valve attached thereto through a resected portion of a papillary muscle. The fixture may further include first and second side panels disposed at opposite sides of the internal panel. The first and second papillary attachment elements may each have a control rod extending through the respective first and second side panels.

A method for applying liquid pressure to resected tissue may include coupling a resected mitral valve to an internal panel extending between first and second chambers of a fixture, the resected mitral valve having a posterior leaflet, an anterior leaflet, and tendinae chordae each attached at a first end to the posterior leaflet or the anterior leaflet. The method may also include attaching a second end of each of the tendinae chordae to one of first and second spaced apart papillary attachment elements, such that a first group of the tendinae chordae are attached to the first papillary attachment element, and a second group of the tendinae chordae are attached to the second papillary attachment element. The method may also include moving at least one of the first and second papillary attachment elements relative to the internal panel in at least one degree of freedom. The method may also include inserting an elongated catheter assembly into at least one of the first and second chambers through an introducer.

The method may also include using the elongated catheter assembly to install a clip onto at least one of the posterior and anterior leaflets of the resected mitral valve. The papillary attachment elements may each be at least partially disposed inside the first chamber, and the inserting step may include inserting the elongated catheter assembly into the first chamber through the introducer, such that the clip is delivered to the resected mitral valve through the first chamber. The papillary attachment elements may each be at least partially disposed inside the first chamber, and the inserting step may include inserting the elongated catheter assembly into the second chamber through the introducer, such that the clip is delivered to the resected mitral valve through the second chamber.

The attaching step may include attaching each of the tendinae chordae to the papillary attachment elements through a resected portion of a papillary muscle. The moving step may include moving first and second control rods of the respective first and second papillary attachment elements, the first and second control rods extending through respective first and second side panels of the fixture disposed at opposite sides of the internal panel. The method may also include pumping liquid through the resected mitral valve.

The method may also include, during the pumping step, using the elongated catheter assembly to install a clip onto at least one of the posterior and anterior leaflets of the resected mitral valve. The papillary attachment elements may each be at least partially disposed inside the first chamber, and the pumping step may include alternatingly pumping high pressure liquid flow into the first chamber and low pressure liquid flow into the second chamber. During the pumping step, the resected mitral valve may alternatingly close and open in response to the alternating pumping of high pressure liquid flow into the first chamber and low pressure liquid flow into the second chamber, respectively.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIGS. 2B and 2C are a perspective view and a longitudinal cross-sectional view of one embodiment of a handle suitable for controlling the device of FIG. 2A, shown with the buttons positioned to correspond to the positions of the components of the device shown in FIG. 2A;

FIG. 3 is a perspective view of the distal portion of the device of FIG. 2A, shown with the containment tube deployed;

FIG. 10A is a view similar to FIG. 8A, but shown with the retaining arm in the retracted position;

FIG. 10B is a view similar to FIG. 8A, but shown with the clip in a partially-deployed position;

FIG. 10C is a diagrammatic view of the clip and the posterior mitral valve leaflet of FIG. 10B, shown with the clip in a partially-deployed position;

FIG. 10D is a longitudinal cross-sectional view of the handle of FIG. 2B, shown with the buttons positioned to correspond to the positions of the components of the device shown in FIG. 10A;

FIG. 11A is a diagrammatic top perspective view of a simulated environment for repair of heart valve leaflet tissue;

DETAILED DESCRIPTION

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
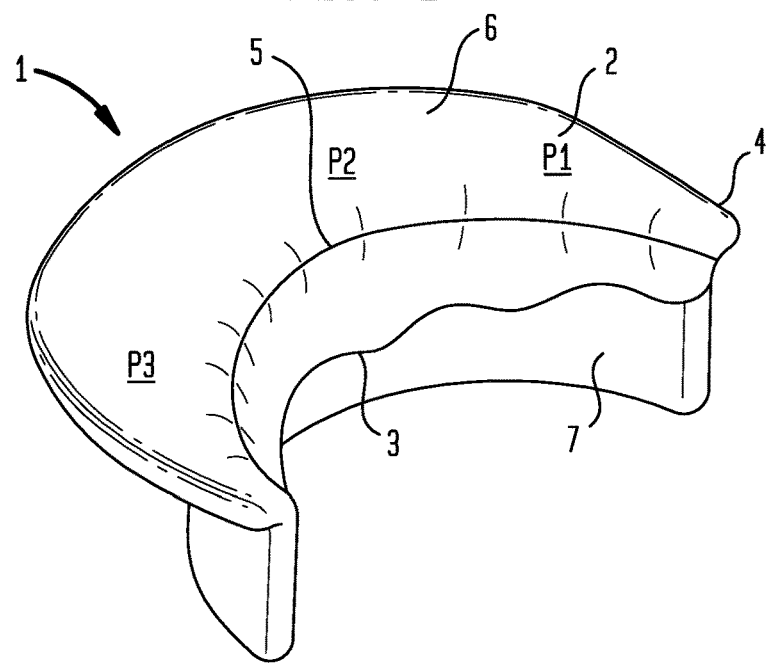
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2A:
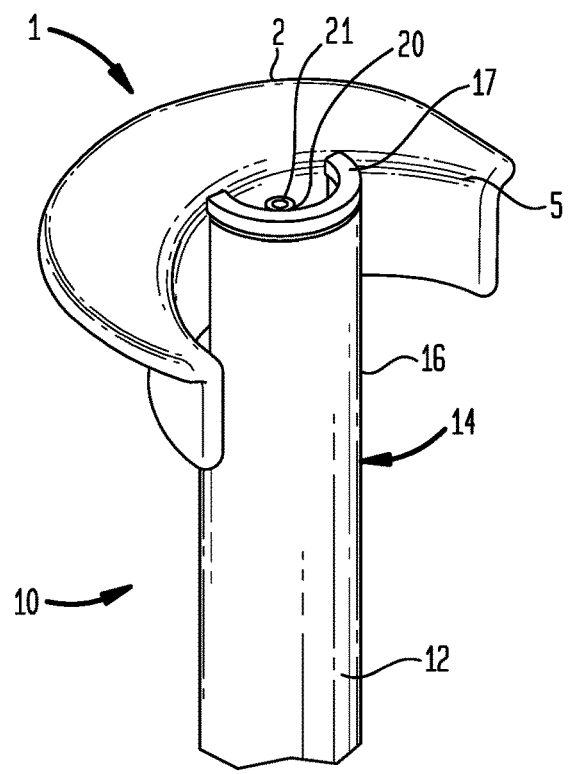
FIG. 2A is a perspective view of the distal portion of one embodiment of a device for transcatheter gathering of heart valve leaflet tissue, engaged with the posterior leaflet of the mitral valve of FIG. 1.

Referring to FIG. 2A, an exemplary device 10 for transcatheter gathering of heart valve leaflet tissue includes an elongated catheter assembly 12 adapted to be inserted through the apex of a human heart so that a distal portion 14 of the catheter assembly may reach the patient's mitral valve 1 for repair thereof.

The catheter assembly 12 includes a containment tube 20 disposed within an outer tube 16 and longitudinally slidable therein between a retracted position within the outer tube and a deployed position in which a distal tip 21 of the containment tube protrudes distally beyond the distal edge 17 of the outer tube (FIG. 3). In a particular embodiment, the outer tube 16 may be made of one or more echogenic materials, so that the outer tube may be more easily visualized inside a patient using three-dimensional echocardiography.

Figure 4A:
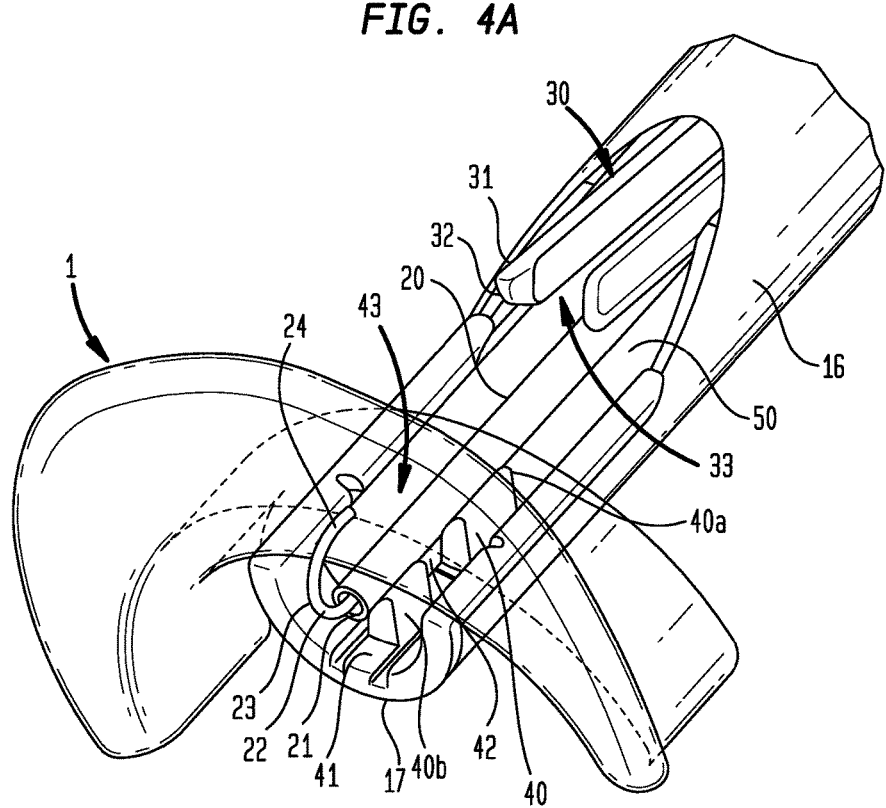
FIGS. 4A and 4B are a perspective view and a longitudinal cross-sectional view of the distal portion of the device of FIG. 2A, shown with the hook deployed.
Figure 4B:
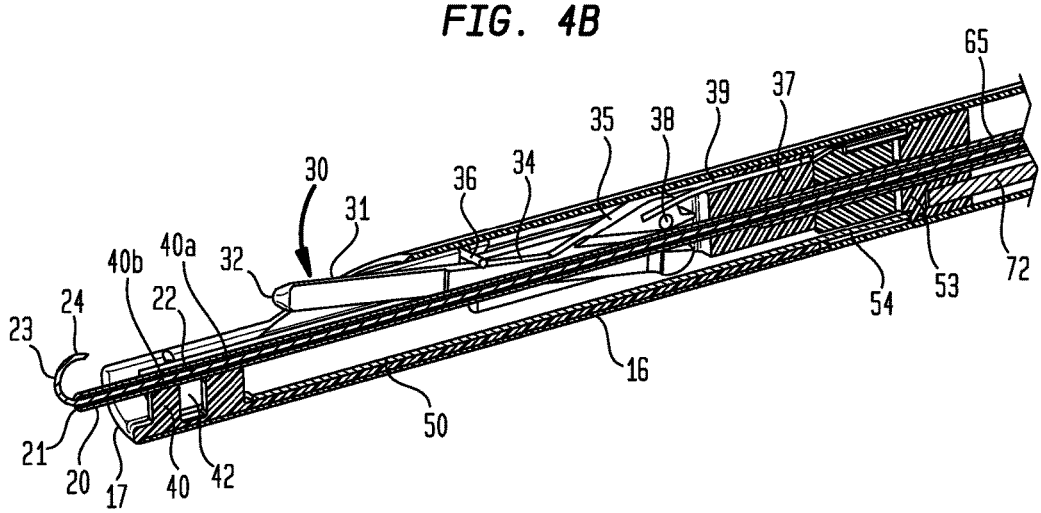

The catheter assembly 12 further includes a capture tool in the form of a grasping wire 22 (FIGS. 4A and 4B) that is longitudinally slidable within the containment tube 20 between a retracted position substantially entirely within the lumen of the containment tube (FIGS. 2 and 3), and a deployed position in which a distal portion 23 of the grasping wire protrudes from the distal tip of the containment tube (FIGS. 4A and 4B). The grasping wire 22 may have a linear configuration when fully retracted within the containment tube 20 and the distal portion 23 thereof may assume the shape of a hook 24 when deployed from the containment tube. In that regard, the grasping wire 22 may be formed from a memory metal or a strong, resilient metal or polymer that will cause the hook 24 to form automatically when deployed.

Figure 8A:
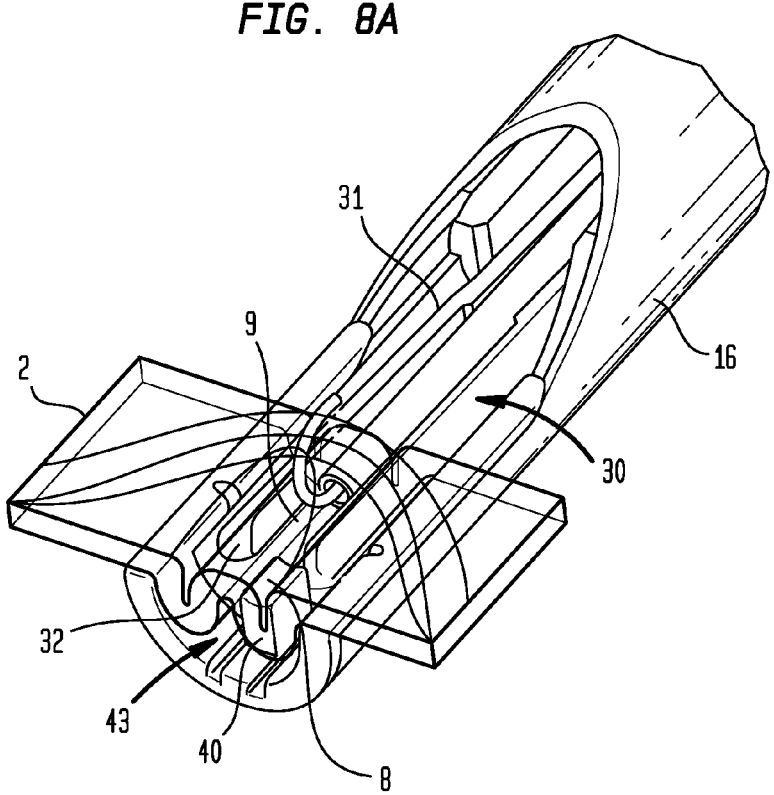
FIGS. 8A and 8B are a perspective view and a longitudinal cross-sectional view of the distal portion of the device of FIG. 2A, shown with the hook in the partially-retracted position and the fork in the tissue-capturing position.

The catheter assembly 12 further includes a clamping member in the form of a fork 30 (FIGS. 4A and 4B) that is longitudinally slidable within the outer tube 16 between an initial or retracted position (FIG. 4A) and a tissue-capturing position (FIG. 8A). The fork 30 includes two tines 31 having respective ends 32, the tines being spaced apart from one another by an internal gap 33. The fork 30 further includes first cam surfaces 34 that are the top surfaces of the tines 31 and a second cam surface 35 located proximally of the tines. The cam surfaces 34 and 35 are adapted to cooperate with a pin 36 attached to the outer tube 16 and orientated substantially orthogonal to the longitudinal direction of travel of the fork 30 to control transverse movement of the fork relative to the outer tube 16, as will be explained below.

At its distal end 17, the outer tube 16 has an open side that provides clearance for the fork 30 to move away from the closed side 41 of the outer tube. A tissue support in the form of an anvil 40 (FIGS. 4A and 4B) is mounted on the closed side 41 of the outer tube 16 so as to lie between the closed side 41 and the containment tube 20 when the containment tube is in the deployed position. The anvil 40 has a proximal portion 40a and a distal portion 40b, with a gap 42 defined therebetween. The widths of the portions 40a and 40b are such that the anvil 40 may be received between the tines 31 of the fork 30 during the use of the device 10 to repair the valve leaflet.

Figure 8B:
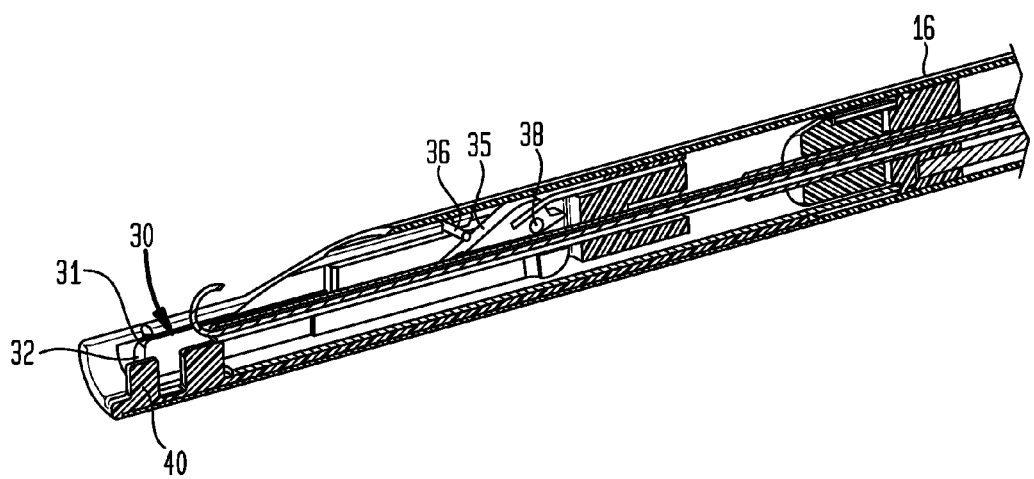
Figure 8C:
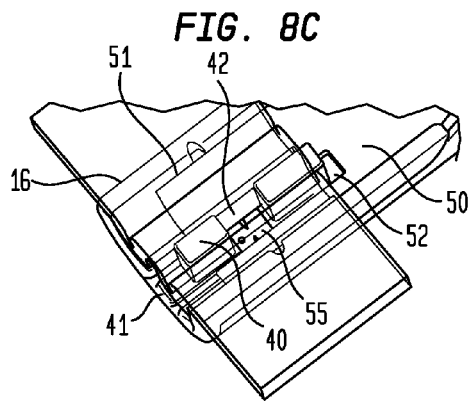
FIG. 8C is a view similar to FIG. 8A, but with portions removed to illustrate the interior of the distal portion.
Figure 9:
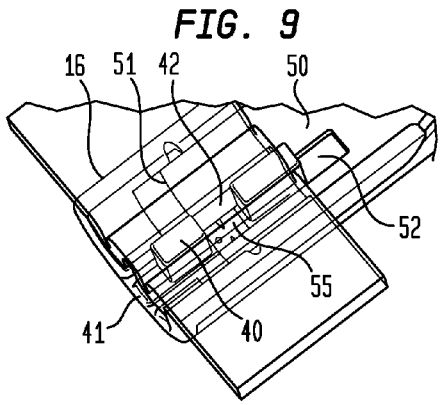
FIG. 9 is a view similar to FIG. 8C, but shown with the retaining arm in a partially-retracted position.

The catheter assembly 12 further includes a retaining arm 50 (FIGS. 4A and 4B) disposed within the outer tube 16 and longitudinally slidable therein between an initial position (FIG. 8C) and a retracted position (FIG. 10A). The retaining arm 50 includes a pair of fingers 51 separated by an elongated slot 52. The slot 52 is sized to receive the anvil 40 when the retaining arm 50 is in the initial position shown in FIG. 8C. In this initial position, the fingers 51 lie on either side of the anvil 40 and engage a clip 55 disposed within the gap 42, holding it in place against the closed side of 41 of the outer tube 16. The retraction of the retaining arm 50 releases the clip 55 for application to tissue.

The clip 55 (FIG. 10A) may be made of a memory metal and may be biased to curl into a substantially round configuration (FIG. 10B) when the retaining arm 50 is retracted proximally and the fingers 51 no longer overlie the clip. A prong 56 at each end of the clip 55 is adapted to become embedded in the leaflet tissue when the clip is deployed.

Referring now to FIGS. 2B and 2C, the device 10 further includes a handle 60 at the proximal end 18 of the outer tube 16. The handle 60 includes a first button 61, a second button 64, and a third button 66 for controlling the operation of the containment tube 20, the grasping wire 22, the fork 30, and the retaining arm 50. The first button 61 has a first portion 62 and a second portion 63 that are moveable longitudinally relative to the handle 60 and relative to one another. The first portion 62 is attached to the containment tube 20, such that sliding movement of the first portion in a proximal or distal direction results in a corresponding sliding movement of the containment tube. The second portion 63 is attached to the grasping wire 22, such that sliding movement of the second portion in a proximal or distal direction results in a corresponding sliding movement of the grasping wire. The containment tube 20 and the grasping wire 22 may be moved together by the simultaneous movement of the first and second portions of the button 61. Alternatively, the containment tube 20 and the grasping wire 22 may be moved independently of one another by moving one of the portions of the button 61 while the other portion remains stationary. For example, sliding the second portion 62 distally while the first portion 63 remains stationary advances the grasping wire 22 out from the containment tube 20, resulting in deployment of the hook 24.

The second button 64 is moveable longitudinally relative to the handle 60 for controlling the movement of the fork 30 relative to the outer tube 16. The second button 64 is attached to one end of a linkage 65, the other end of which is attached to a coupling block 37 (FIG. 4B) positioned in the distal portion 14 of the catheter assembly 16. The coupling block 37, in turn, is coupled to the fork 30 via a pivot pin 38 and a spring 39 that extends between the fork and the coupling block. The spring 39 is biased to rotate the fork 30 about the pivot pin 38 so that the tines 31 of the fork move laterally away from the closed side 41 of the outer tube 16.

The third button 66 has a trigger shape and is connected at one end to the handle 60 by a pivot pin 67 that allows for movement of the button in a lateral direction relative to the longitudinal axis of the handle for controlling the movement of the retaining arm 50 relative to the outer tube 16. A spring 68 biases the third button 66 to return to its initial position (FIG. 2C) after the button has been actuated (FIG. 10D). The opposite end 69 of the third button 66 is pivotally coupled to a linkage assembly including a first linkage 70, a second linkage 71, and a third linkage 72, all of which are pivotally connected to one another in series. The third linkage 72 is attached to a coupling block 53 positioned in the distal portion 14 of the catheter assembly 12. The coupling block 53, in turn, is attached to a proximal end 54 (FIG. 4B) of the retaining arm 50, such that actuation of the third button 66 may cause the third linkage 72 to slide proximally to retract the retaining arm and thereby deploy the clip 55 (FIG. 10B).

Figure 8D:
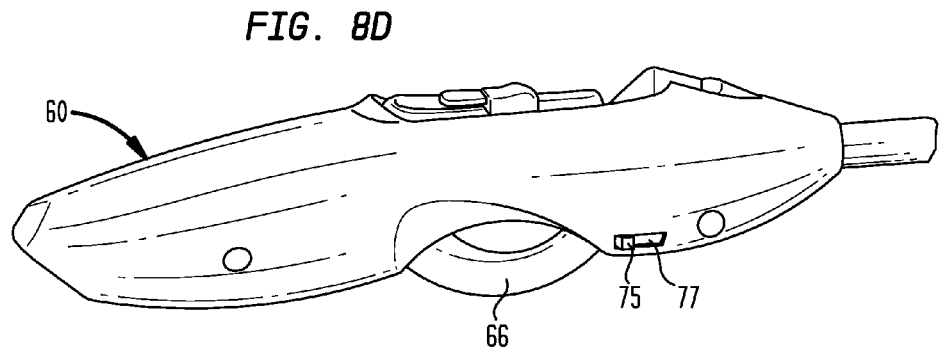
FIGS. 8D and 8E are a perspective view and a longitudinal cross-sectional view of the handle of FIG. 2B, shown with the buttons positioned to correspond to the positions of the components of the device shown in FIG. 8A.
Figure 8E:
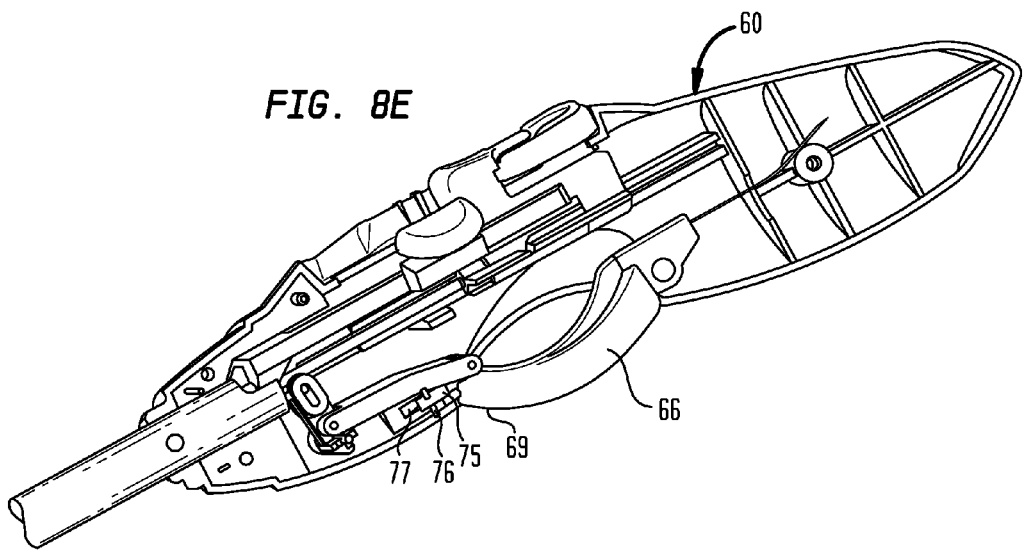

Referring again to FIGS. 2B and 2C, a safety catch 75 may be connected to the handle 60 by a pivot pin 76, such that the safety catch may rotate between a locked position (FIGS. 8D and 8E) that prevents actuation of the third button 66 and an unlocked position (FIG. 10D) that frees the third button for actuation.

To use the device 10 for transcatheter gathering of heart valve leaflet tissue, a user may first actuate the third button 66 of the handle 60 to retract the fingers 51 of the retaining arm 50 proximally of the gap 42 between the anvil portions 40a and 40b (FIG. 10B). A clip 55 may then be loaded into the gap 42, and the third button 66 released. The spring 68 will then bias the third button 66 back to its initial position, whereupon the retaining arm 50 will slide distally until the fingers 51 thereof cover the clip 55 and hold it in place.

Next, referring to FIG. 2A, the distal portion 14 of the catheter assembly 12 may be inserted into a patient through the apex of the heart, for example, into the left ventricle, so that the distal portion extends between the posterior leaflet 2 and the anterior leaflet 3 of the mitral valve 1. As shown in FIG. 2A, the distal edge 17 of the outer tube 16 may be disposed approximately at the coaption line 5 of the mitral valve 1, with the open side of the outer tube 16 facing the posterior leaflet 2 (alternatively, if the anterior leaflet 3 is being repaired, the open side of the outer tube may face the anterior leaflet). In a particular embodiment, the distal edge 17 of the outer tube 16 may be guided to a position at the coaption line 5 using the assistance of three-dimensional echocardiography to visualize the outer tube or other components of the catheter assembly 12.

Then, referring to FIG. 3, the containment tube 20 may be deployed by sliding the first and second portions 62 and 63 of the first button 61 together distally from an initial position (shown in FIG. 2B) to a deployed position. The distal movement of the first button 61 moves the tip 21 of the containment tube 20 beyond the distal end 17 of the outer tube 16, such that the tip 21 extends above the coaption line 5.

Figure 4C:
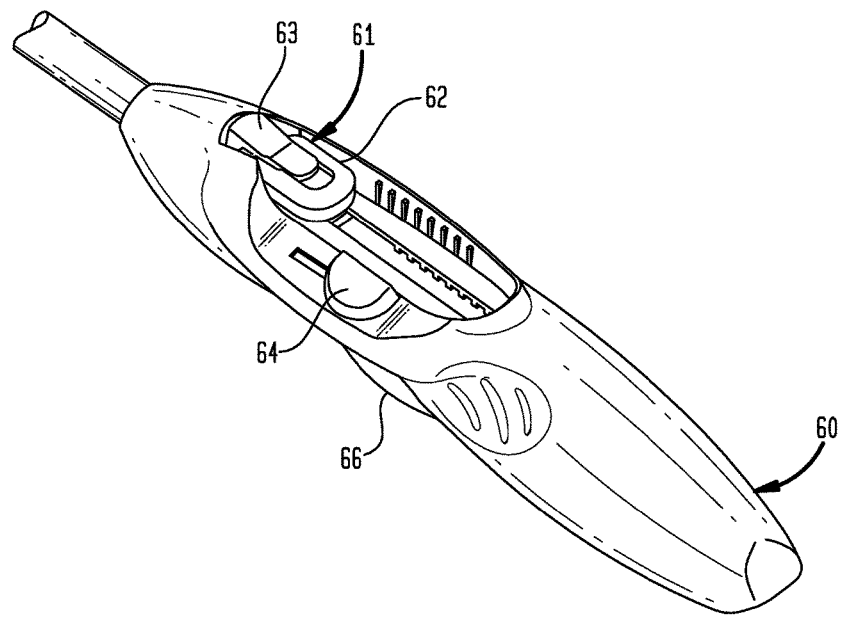
FIGS. 4C and 4D are a perspective view and a longitudinal cross-sectional view of the handle of FIG. 2B, shown with the buttons positioned to correspond to the positions of the components of the device shown in FIG. 4A.
Figure 4D:
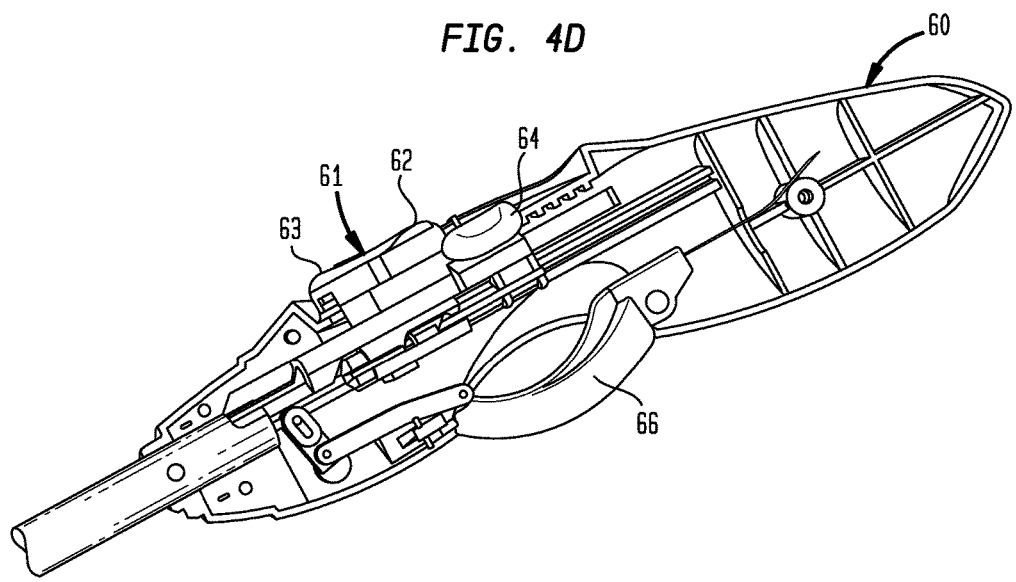

Referring to FIGS. 4A and 4B, the hook 24 may then be deployed to an extended position by sliding the second portion 63 of the first button 61 distally relative to the first portion 62 from an initial position (shown in FIG. 2B) to a deployed position (shown in FIGS. 4C and 4D). The distal movement of the second portion 63 relative to the first portion 62 moves the distal portion 23 of the grasping wire 22 out of the containment tube 20. No longer being constrained by the containment tube 20, the distal portion 23 of the grasping wire 22 may assume the curved shape of the hook 24.

Figure 5A:
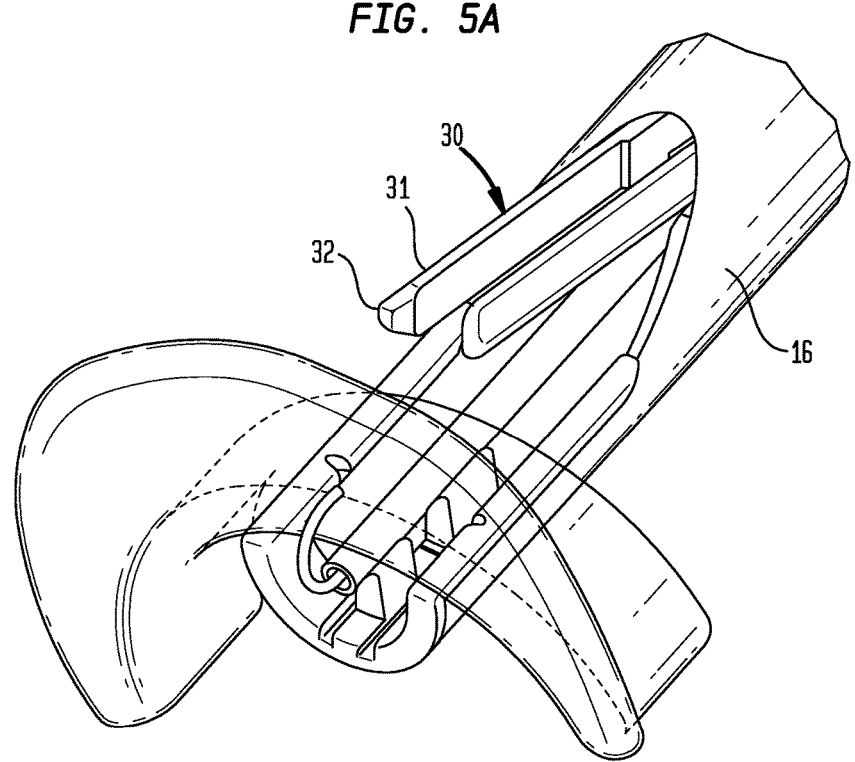
FIGS. 5A and 5B are a perspective view and a longitudinal cross-sectional view of the distal portion of the device of FIG. 2A, shown with the fork partially deployed.
Figure 5B:
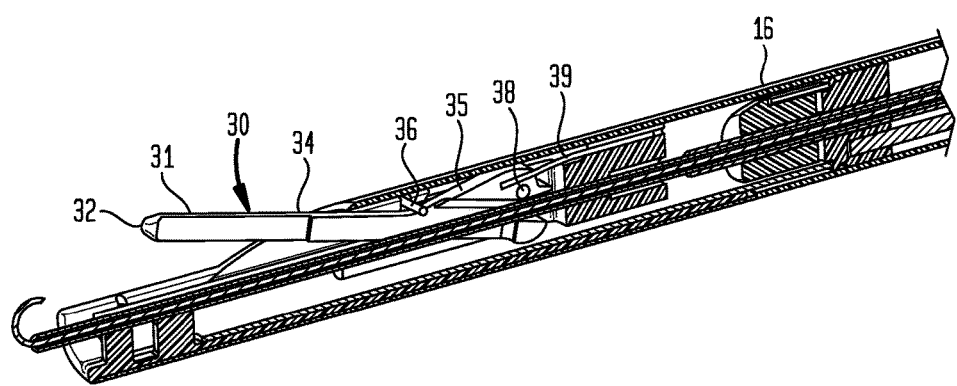

The fork 30 may then be partially deployed by sliding the second button 64 distally from an initial position (shown in FIG. 4C) to an intermediate position (not shown). As shown in FIGS. 5A and 5B, the distal movement of the second button 64 moves the fork 30 distally relative to the outer tube 16. As the fork 30 moves distally, the spring 39 will continue to exert a rotational force to the fork (in the clockwise direction of FIG. 5B), forcing the first cam surface 34 of each tine 31 against the pin 36. The distal movement of the cam surface 34 against the pin 36 will allow the ends 32 of the tines 31 to move gradually away from the closed side 41 of the outer tube 16 and away from the anvil 40.

Figure 6A:
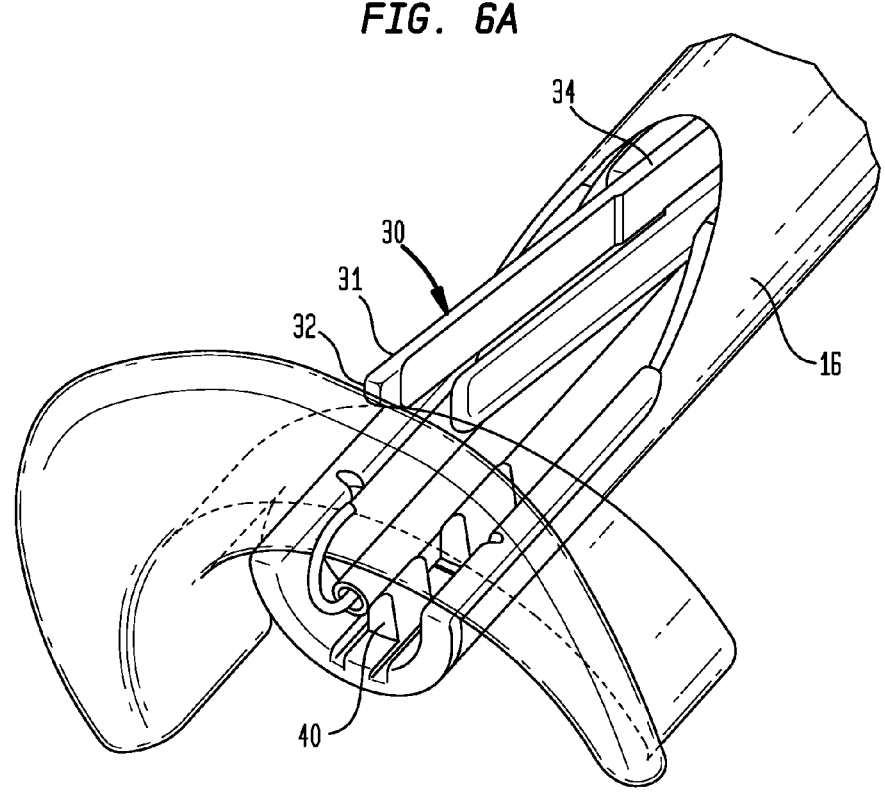
FIGS. 6A and 6B are a perspective view and a longitudinal cross-sectional view of the distal portion of the device of FIG. 2A, shown with the fork in the support position.
Figure 6B:
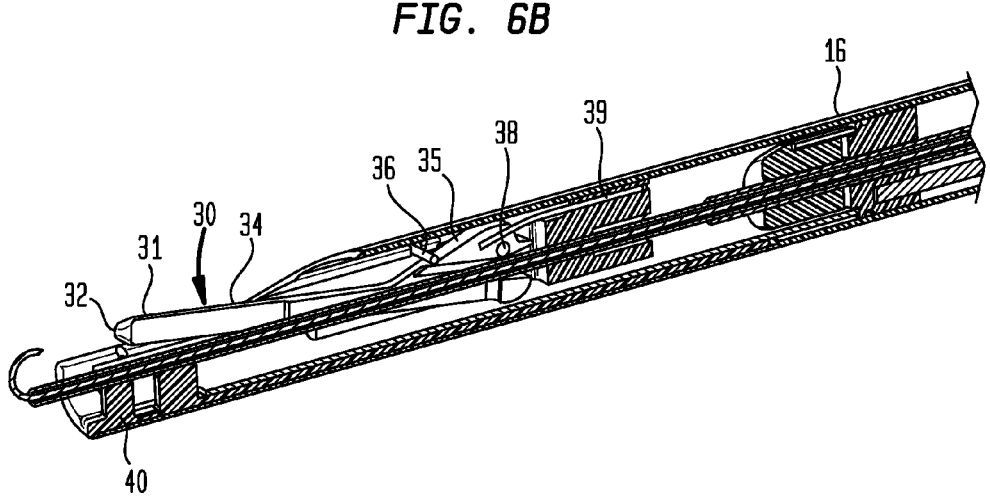
Figure 6C:
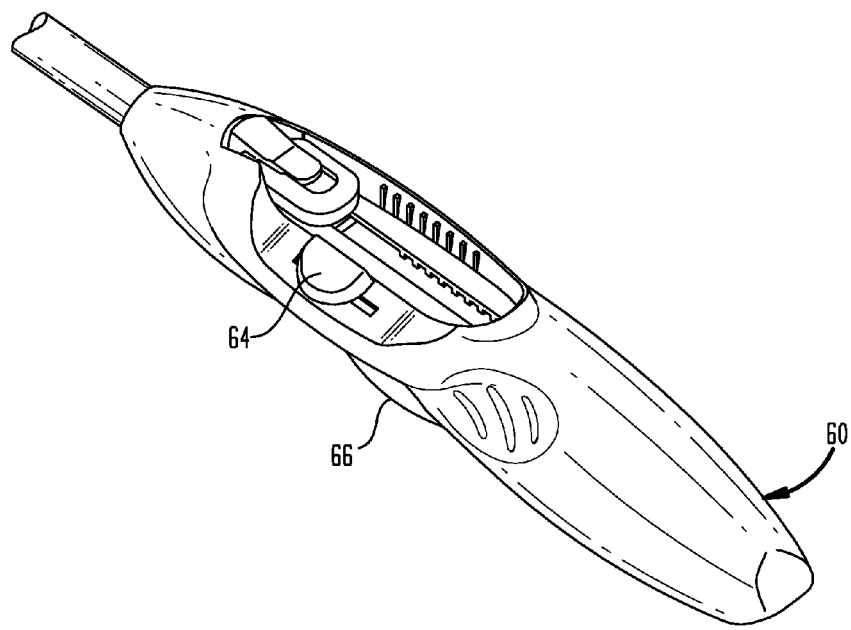
FIGS. 6C and 6D are a perspective view and a longitudinal cross-sectional view of the handle of FIG. 2B, shown with the buttons positioned to correspond to the positions of the components of the device shown in FIG. 6A.
Figure 6D:
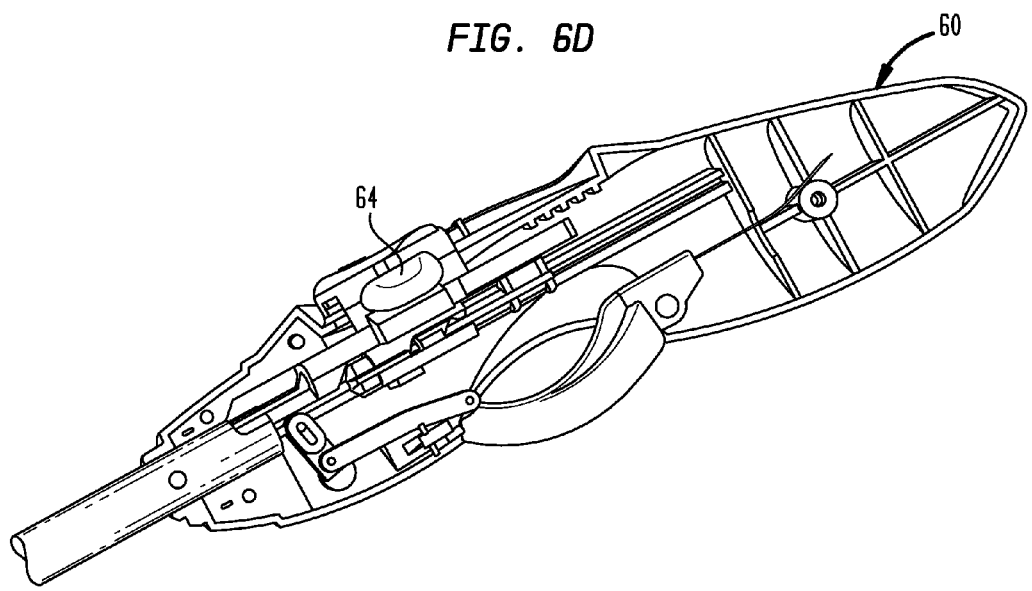

The fork 30 may continue to be deployed toward an open position by further movement of the second button 64 in the distal direction. As the fork 30 advances, the ends 32 of the tines 31 will continue to move laterally away from the closed side 41 of the outer tube 16 until the pin 36 reaches the intersection of the cam surfaces 34 and 35. Because the cam surface 35 is at a different angle than the cam surface 34, the interaction of the pin 36 and the cam surface 35 will exert a rotational force in the opposite direction as the fork 30 continues to advance. That is, as the fork 30 moves further distally, the pin 36 will exert a downward force tending to rotate the fork in the opposite direction (i.e., counterclockwise in FIG. 6B). As this latter force is greater than the rotation force exerted by spring 39, further distal movement of the fork 30 will cause the ends 32 of the tines 31 to move laterally towards the closed side 41 of the outer tube 16 and towards the anvil 40.

Figure 7A:
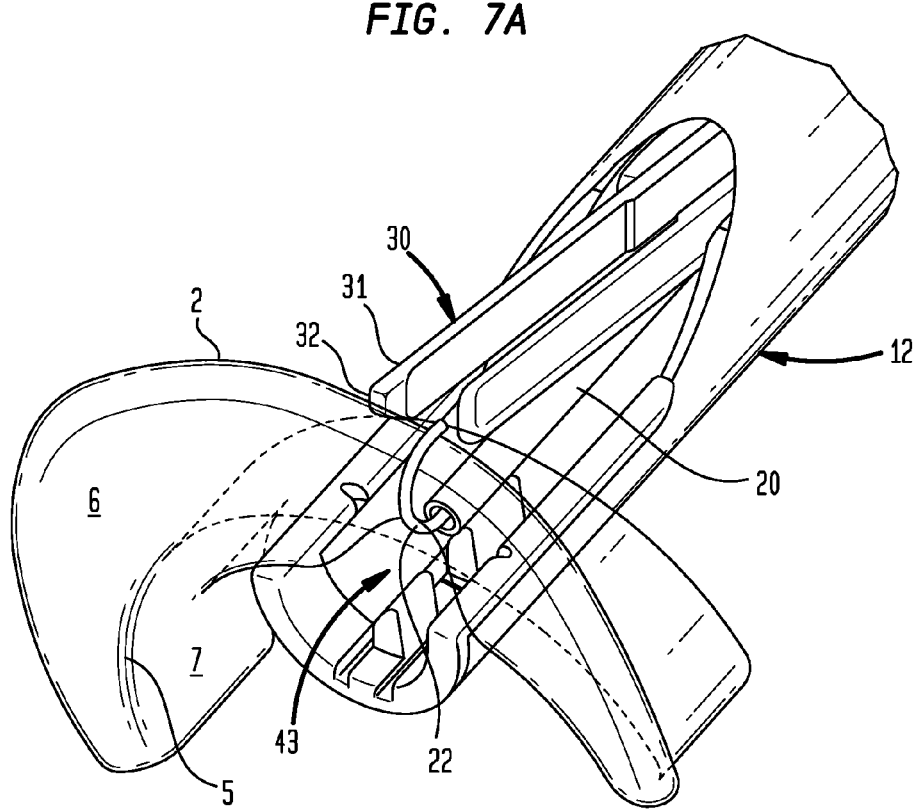
FIG. 7A is a perspective view of the distal portion of the device of FIG. 2A, shown with the hook in the partially-retracted position and the fork in the support position.
Figure 7B:
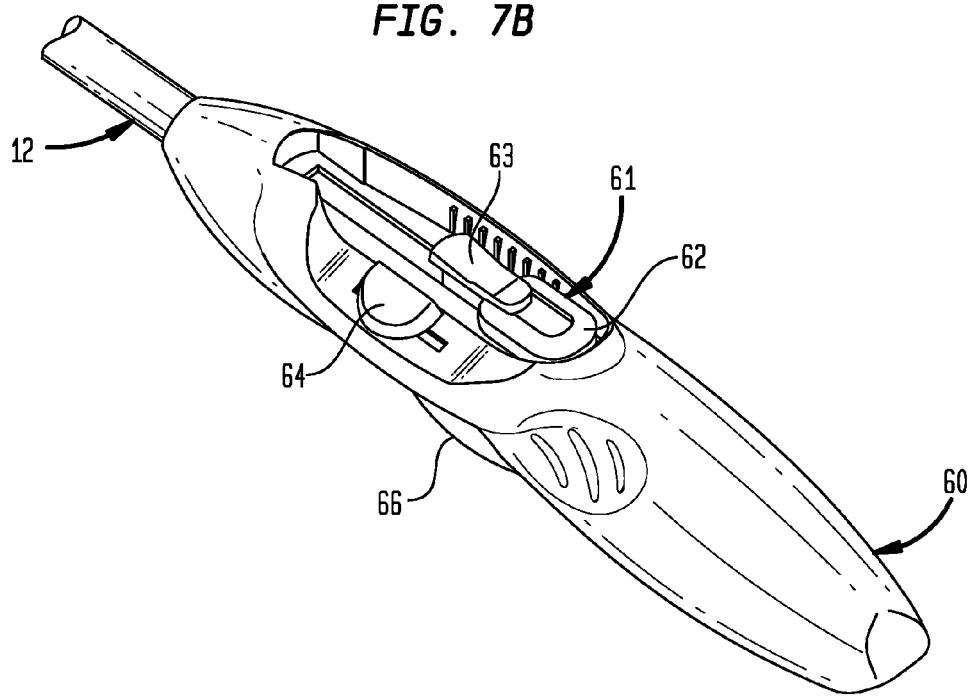
FIG. 7B is a perspective view of the handle of FIG. 2B, shown with the buttons positioned to correspond to the positions of the components of the device shown in FIG. 7A.

Referring to FIGS. 7A and 7B, the hook 24 may be partially retracted against the tissue of the posterior leaflet 2 by sliding the first and second portions 62 and 63 of the first button 61 together proximally (FIG. 7B). The proximal movement of the first button 61 partially retracts both the containment tube 20 and the grasping wire 22, such that the hook 24 engages against the upper surface 6 of the posterior leaflet 2 and pulls tissue of the leaflet into the space 43 between the containment tube and the tines 31 of the fork 30.

The tissue captured in the space 43 may be clamped between the anvil 40 and the tines 31 of the fork 30 by further sliding of the second button 64 distally to the fully deployed position. The further distal movement of the second button 64 moves the fork 30 further distally relative to the outer tube 16. As the fork 30 advances further toward a closed position adjacent the anvil 40, the interaction of the second cam surface 35 with the pin 36 will force the tines 31 of the fork toward the anvil and the closed side 41 of the outer tube 16, squeezing the captured tissue 9 therebetween. Continued movement of the fork 30 toward the anvil 40 will force the captured tissue 9 into the space 33 between the tines 31, and into the spaces between the tines and the closed side 41 of the outer portion 16. A W-shaped pleat 8 (FIG. 10C) will thus be formed in the captured tissue 9, with the raised center portion of the W overlying the anvil 40, and the two lower portions of the W lying between the tines 31 and the closed side 41 of the outer tube 16. By forming a W-shaped pleat 8, most or all of the portion of the posterior leaflet 2 that is billowed, loose, or floppy may be gathered and tightened.

With the tissue captured, the retaining arm 50 may be retracted by releasing the catch 75 and actuating the third button 66 by depressing it toward the handle 60. The retaining arm 50 may be retracted until the fingers 51 thereof are proximal of the gap 42 in the anvil 40 (FIG. 10B). At this juncture, the fingers 51 will no longer overlie the clip 55, such that the two prongs 56 of the clip will be free to spring away from the closed surface 41 of the outer tube 16 and become embedded in the captured tissue 9 of the posterior leaflet 2, thereby securing the tissue in the pleated form.

At this point, the clip 55 may be only partially engaged into the posterior leaflet 2 because the tines 31 of the fork 30 are positioned within the folds of the pleat 8. In a particular example, the clip 55 may be engaged in the lower portion 7 of the posterior leaflet 2 close to the coaption line 5. Optionally, a suture, such as the suture 258 described below with respect to FIGS. 16A and 16B, may extend from the clip 55 to the catheter assembly 12 so that the clip may be retrieved using the device 10, for example, if the clip has been installed at a sub-optimal location in the posterior leaflet 2 or does not become adequately embedded in the tissue. A user may desire to disengage the clip from the tissue and deploy another one.

After the clip 55 has been adequately secured in the tissue of the posterior leaflet 2, the device 10 may be withdrawn from the patient. To withdraw the device 10, the hook 24 may first be withdrawn from engagement with the posterior leaflet 2 by retracting the second portion 63 of the first button 61 relative to the first portion 62 thereof. This action causes the hook 24 to straighten as the grasping wire 22 retracts into the containment tube 20.

Next, the fork 30 may be withdrawn from within the clip 55. To withdraw the fork 30, the second button 64 may be moved proximally, thereby moving the fork proximally relative to the outer tube 16. While the fork 30 moves proximally, the spring 39 will exert a rotational force to the fork (in the clockwise direction of FIG. 8B), forcing the second cam surface 35 against the pin 36. The proximal movement of the cam surface 35 against the pin 36 will allow the ends 32 of the tines 31 to move gradually away from the closed side 41 of the outer tube 16 and away from the anvil 40. As the fork 30 continues to move proximally, the ends 32 of the tines 31 will continue to move laterally away from the closed side 41 of the outer tube 16 until the pin 36 reaches the intersection of the cam surfaces 34 and 35. Because the cam surface 35 is at a different angle than the cam surfaces 34, the interaction of the pin 36 and the cam surfaces 34 will exert a rotational force in the opposite direction as the fork 30 continues to move proximally. That is, as the fork 30 moves further proximally, the pin 36 will exert a downward force tending to rotate the fork in the opposite direction (i.e., counterclockwise in FIG. 5B). As this latter force is greater than the rotation force exerted by spring 39, further proximal movement of the fork 30 will cause the ends 32 of the tines 31 to move laterally towards the closed side 41 of the outer tube 16, thereby enabling the fork 30 to retract into the outer tube.

Once the fork 30 has disengaged from within the clip 55, the two prongs 56 of the clip may become more tightly embedded in the posterior leaflet 2, such that the two prongs may cross one another, thereby allowing the clip to extend along an arc that is greater than 360 degrees. Finally, the catheter assembly 12 may be withdrawn from the patient through the apex of the heart. The procedure described above may be repeated to apply one or more additional clips 55 onto the same posterior leaflet 2.

Figure 11B:
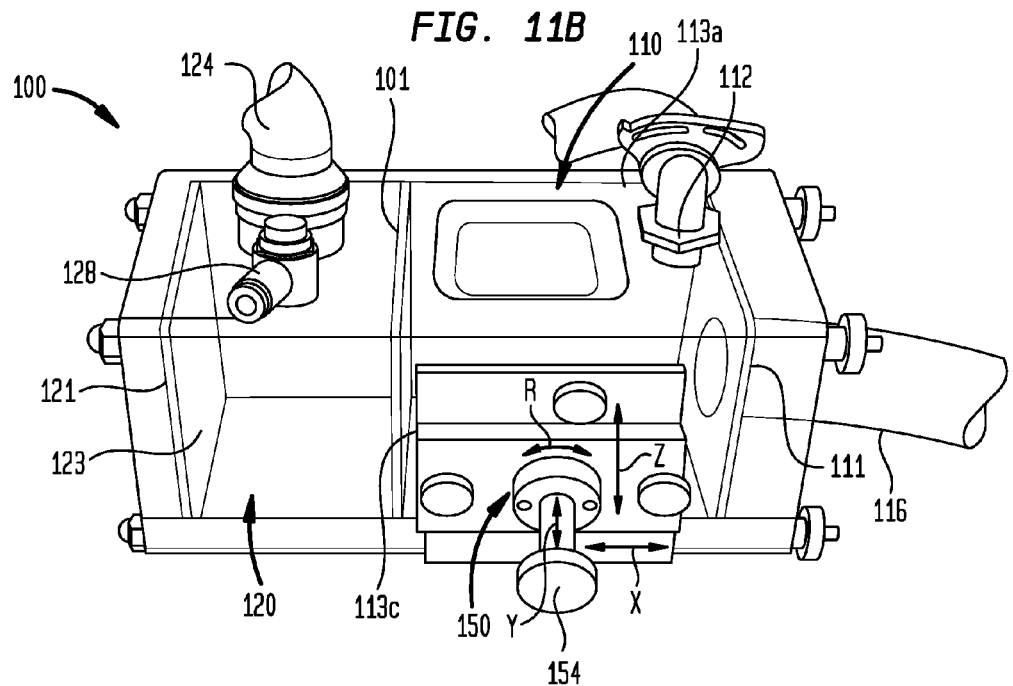
FIG. 11B is a diagrammatic side perspective view the simulated environment of FIG. 11A.

Referring now to FIGS. 11A and 11B, an exemplary repair simulation apparatus 100 may include a left ventricle 110, a left atrium 120, a mitral valve 130 assembled between the left ventricle and the left atrium, and a pumping system 140 to provide liquid flow through the apparatus.

The simulation apparatus 100 may be used to train users such as surgeons to deploy to repair a posterior leaflet of the mitral valve of a live human patient. The simulation apparatus 100 may also be used for deployment testing of various designs of repair devices 10 and clips 55 in modeled mitral valves having various configurations (e.g., the severity of mitral valve prolapse, the degree of tension present in the chordae tendinae, etc). In this regard, by way of example, the simulation apparatus 100 is adapted to receive the distal portion 14 of the repair device 10 (FIG. 2A) therein for installation of a clip 55 (FIG. 10C) onto the mitral valve 130.

As can be seen in FIG. 11A, the left ventricle 110 may have a polygonal configuration such as a box-like configuration, or it may alternatively have a non-polygonal configuration. The mitral valve 130 may be mounted to an interior panel 101 of the apparatus 100. The mitral valve 130 may serve as a first inlet port of the left ventricle 110, through which liquid may flow into the left ventricle from the left atrium 120. The left ventricle 110 may have a second inlet port 112 configured to receive liquid flow therethrough from the pumping system 140. The second inlet port 112 may be mounted within a top panel 113a of the left ventricle 110.

The left ventricle 110 may have an aortic valve 114 that may serve as an outlet port configured to receive liquid flow therethrough to the pumping system 140. The aortic valve 114 may be mounted within a bottom panel 113b of the left ventricle 110 opposite the top panel 113a. The aortic valve 114 may be a bicuspid mechanical valve that automatically opens when the pressure of a liquid inside the left ventricle 110 exceeds the pressure in the low pressure chamber 141 and that automatically closes when pressure of a liquid inside the left ventricle drops below the pressure in the low pressure chamber.

An end panel 111 of the left ventricle 110 may have an introducer 116 mounted thereto and configured to receive, by way of example, the distal portion 14 of the transapical repair device 10 therethrough. As shown in FIG. 11A, the end panel 111 may be located at the opposite end of the left ventricle 110 from the interior panel 101. The introducer 116 may include an internal gasket (not shown) configured to create a seal around the device 10 while it extends within the left ventricle 110. The introducer 116 may simulate the approximate location of the left ventricular apex of the heart relative to the mitral valve 130.

Still referring to FIG. 11A, the left atrium 120 may have a polygonal configuration such as a box-like configuration, or it may alternatively have a non-polygonal configuration. The left atrium 120 may have an inlet port 122 configured to receive liquid flow therethrough from the pumping system 140. The inlet port 122 may be mounted within any of the side panels 123 of the left atrium 120. The mitral valve 130 may serve as an outlet port of the left atrium 120, through which liquid may flow out of the left atrium to the left ventricle 110. Therefore, the same mitral valve 130 may serve as an inlet port of the left ventricle 110 as well as an outlet port of the left atrium 120, because liquid can flow out of the left atrium and into the left ventricle through the mitral valve.

The left atrium 120 may have a first introducer 124 mounted within any of the side panels 123. The first introducer 124 may be configured to receive the distal portion of a three-dimensional echocardiography probe therethrough, which may be used so that the distal portion of a transfemoral repair device may be more easily visualized inside of the apparatus 100 using three-dimensional echocardiography.

The left atrium 120 may have a second introducer 126 mounted within an end panel 121 of the left atrium. As shown in FIG. 11A, the end panel 121 may be located at the opposite end of the left atrium 120 from the interior panel 101. The second introducer 126 may be configured to receive the distal portion of a transfemoral repair device similar to the distal portion 14 of the device 10 therethrough, so that the distal portion of the transfemoral repair device may approach the mitral valve 130 from the left atrium 120. The introducers 124 and 126 may each include an internal gasket (not shown) configured to create a seal around a transcatheter device while it extends within the left atrium 120. The left atrium may also have a gas purge valve mounted within any of the side panels 123 for purging gas that may be present within the left atrium 120.

The mitral valve 130 may include a resected human or animal mitral valve similar to the mitral valve 1 described above with reference to FIG. 1. The mitral valve 130 preferably is oriented with the coaption line 135 extending in a direction generally parallel to the top and bottom panels 113a and 113b of the left ventricle 110. The mitral valve 130 is oriented with the bottom surface 138 of each of the posterior leaflet 132 and the anterior leaflet 133 facing into the left ventricle 110.

Figure 12A:
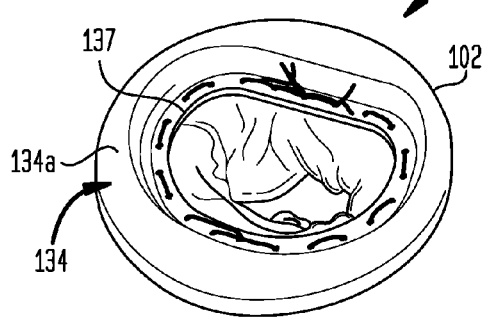
FIG. 12A is a top perspective view of the mitral valve assembly of FIG. 11A.

As can be seen in FIG. 12A, the mitral valve 130 may further include an annular ring 134 that may be configured to permit the mitral valve to be removably installed into an opening 102 of the interior panel 101. In one example, the annular ring 134 may be made of a relatively stiff material, such as a polymer. The annular ring 134 may be in the shape of a ring, and the native annulus 136 (FIG. 12B) of the resected mitral valve may be sutured to the annular ring through apertures extending through the annular ring adjacent an inner edge 137 thereof. The annular ring 134 may comprise a first portion 134a and a second portion 134b joined at the inner edge 137. The annular ring 134 may be installed into the opening 102 of the interior panel 101 of the apparatus 100 such that the first portion 134a is located in the left ventricle and the second portion 134b is located in the left atrium 120. In one example, the annular ring 134 may have an adjustable internal circumference, as described, for example, in U.S. Pat. No. 7,297,150 and U.S. Patent Application Publication No. 2006/0241748, the disclosures of which are hereby incorporated by reference herein.

Referring again to FIG. 11A, the chordae tendinae 131 of each of the posterior leaflet 132 and the anterior leaflet 133 may be attached to a pair of papillary assemblies 150. Each papillary assembly 150 may extend through a corresponding side panel 113c of the left ventricle 110. Each papillary assembly 150 may include a suture plate 152 to which tendinae chordae 131 of the mitral valve 130 may be attached. Each papillary assembly 150 may also include a control rod 154 configured to position the respective suture plate 152 at a desired location and orientation within the left ventricle 110.

Figure 12B:
FIG. 12B is a side view of the mitral valve assembly of FIG. 12A, shown coupled to a papillary suture plate.

As can be seen in FIG. 12B, the tendinae chordae 131 of the mitral valve 130 may be indirectly attached to the suture plate 152 through a resected portion of the native papillary muscle 156 of the heart from which the resected human or animal mitral valve was harvested. Each papillary muscle 156 may be sutured to a corresponding one of the suture plates 152.

Figure 12C:
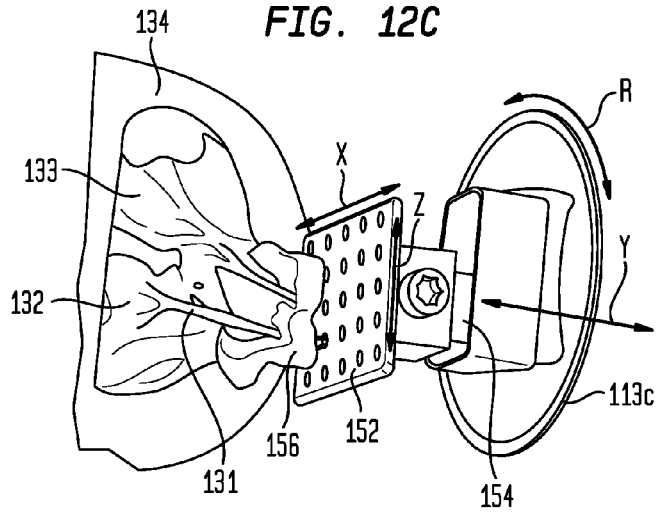
FIG. 12C is a bottom perspective view of the mitral valve assembly of FIG. 12A, shown coupled to a papillary suture plate.

As can be seen in FIG. 12C, each suture plate 152 may be adjusted in four degrees of freedom by the corresponding control rod 154. Each suture plate 152 may be translated along X, Y, and Z linear axes of a Cartesian coordinate system, indicated in FIGS. 11B and 12C, and each suture plate may be rotated about a rotational axis R, also indicated in FIGS. 11B and 12C. In one example, each suture plate 152 may be adjusted in six degrees of freedom by the corresponding control rod 154, such that each suture plate may be translated along X, Y, and Z linear axes of a Cartesian coordinate system and rotated about each of the X, Y, and Z linear axes.

Such adjustment of each suture plate 152 may permit a user to simulate various structural problems of the mitral valve 130 to be repaired. For example, movement of the suture plates 152 along the X axis may cause the chordae tendinae 131 to tighten or loosen, thereby permitting adjustment of the severity of the prolapse condition to be repaired. In another example, rotation of the suture plates 152 along the rotational axis R may cause the chordae tendinae 131 attached to the posterior leaflet 132 to be loosened, while the chordae tendinae attached to the anterior leaflet 133 to be tightened, thereby simulating a floppy posterior leaflet. Alternatively or in addition to adjusting the location and orientation of each suture plate 152, one or more chordae tendinae 131 may be cut or otherwise detached from the corresponding leaflet 132 or 133 to simulate a loose or floppy leaflet condition.

Referring again to FIG. 11A, the pumping system 140 may be configured to pump a liquid (e.g., saline) through the apparatus 100 to simulate blood flowing through the mitral valve 130 and to provide a pressure differential across the mitral valve to close and open the mitral valve. The pumping system 140 may be configured to alternatingly provide: (i) a high pressure liquid pulse (e.g., 190 mmHg) into the left ventricle 110 at the inlet port 112 to close the valve 130, and (ii) a back pressure (e.g., 90 mmHg) into the left atrium 120 at the inlet port 122 to open the valve.

The pumping system 140 may be a partially closed recirculating liquid flow system, and may include a low pressure chamber 141, an open liquid tank 142, a high pressure chamber 143, and a gas pulse generator 144.

The low pressure chamber 141 may be in the form of a vertically oriented tank (e.g., a cylindrical tube) that is adapted to have a top liquid surface near the upper outlet 141c that is at a height H1 above the lower outlet 141b. The back pressure provided at the inlet port 122 of the left atrium 120 is linearly related to the column height of the liquid in the low pressure chamber 141 relative to the inlet port 122. Therefore, the low pressure chamber 141 can made to provide a desired back pressure (e.g., 90 mmHg) by raising or lowering the upper outlet 141c of the low pressure chamber relative to the inlet port 122 of the left atrium 120 until the desired back pressure is achieved.

A downspout 141d of the low pressure chamber 141 has an upper end connected to the upper outlet 141c, and a lower end located in the open liquid tank 142, such that any liquid that rises above the upper outlet 141c will flow through the downspout into the open liquid tank, thereby preventing the back pressure at the inlet port 122 of the left atrium 120 from exceeding the desired maximum value. The low pressure chamber 141 may also have an inlet 141a into which liquid can flow from the aortic valve 114 of the left ventricle 110. The pumping system 140 may include a one-way valve 149a between the inlet 141a and the aortic valve 114 to prevent backflow from the low pressure chamber 141 into the left ventricle 110 through the aortic valve.

The open liquid tank 142 may be in the form of a horizontally oriented tank that is adapted to have a top liquid surface 142a that is at a height H2 above the outlet 142b. The pressure provided at the outlet 142b of the open liquid tank 142 is linearly related to the height of the liquid relative to the outlet 142b. The open liquid tank 142 is configured such that liquid flowing from the low pressure chamber 141 into the open liquid tank does not substantially change the height H2, because the horizontal orientation of the open liquid tank spreads the volume of additional liquid over a large area of the surface 142a. The pumping system is configured so that the liquid surface 142a is at a lower height than the outlet 141b of the low pressure chamber 141. The open liquid tank 142 may be heated to approximately 98° F., so that when the liquid is pumped into the left ventricle 110 and the left atrium 120, the left ventricle and left atrium will have approximately the same temperature as a left ventricle and left atrium in a live human patient.

The high pressure chamber 143 may include an outer chamber 145 surrounded by a rigid outer wall 146, and an inner chamber 147 surrounded by a compliant tube 148 made of a silicon elastomer, for example. A liquid inlet 143a of the high pressure chamber 143 may be in fluid communication with the inner chamber 147, and may be in one-way fluid communication with the outlet 142b of the open liquid tank 142 via a one-way valve 149b between the inlet 143a and the outlet 142b. A liquid outlet 143b of the high pressure chamber 143 may be in fluid communication with the inner chamber 147, and with the inlet 112 of the left ventricle 110. A gas inlet 143c of the high pressure chamber 143 may be in fluid communication with the outer chamber 145, and may be in fluid communication with the gas pulse generator 144. The pumping system is configured so that the highest point of the liquid in the compliant tube 148 is at a lower height than the liquid surface 142a of the open liquid tank 142.

In use, the pumping system 140 may be configured to pump liquid into the left atrium 120 through the inlet port 122 at approximately 70 beats or pulses per minute, providing approximately 5.0 liters per minute into the left atrium, at a mean pressure of approximately 90 mmHg ("low pressure"). The pumping system 140 may also be configured to pump liquid into the left ventricle 110 through the second inlet port 112 at approximately 70 beats or pulses per minute, providing approximately 5.0 liters per minute into the left ventricle, at a mean pressure of approximately 190 mmHg ("high pressure").

The pumping system 140 may be configured to alternatingly pump liquid into the left atrium 120 at low pressure and into the left ventricle 110 at high pressure, such that each of the left atrium and left ventricle receives 70 pulses per minute of liquid. Such alternating pulses may approximately simulate the alternating low and high pressure conditions within the left ventricle that serves to open and close a native mitral valve in a human patient.

Initially, when the pumping system 140 is at rest, the valve 130 is open, because the outer chamber 145 of the high pressure chamber 143 is not pressurized, and because the liquid surface 142a of the open liquid tank 142 is at the same height as the level of water in the low pressure chamber 141, so the back pressure in the left atrium 120 (e.g., 30 mmHg) is equal to the pressure of the left ventricle 110.

To generate a high-pressure liquid pulse (e.g., 190 mmHg) into the inlet port 112 of the left ventricle 110, the gas pulse generator 144 may force a pressurized gas pulse into the gas inlet 143c of the high pressure chamber. Since the gas inlet 143c is in fluid communication with the outer surface of the compliant tube 148, a pulse of pressurized gas entering the outer chamber 145 will squeeze the outer surface of the compliant tube, thereby sharply raising the pressure of the liquid in the inner chamber 147. When the pressure of the liquid in the inner chamber 147 is raised above the pressure at the outlet 142a of the open liquid tank 142, the one-way valve 149b will close, so the pressurized liquid within the inner chamber 147 will be forced to flow out of the liquid outlet 143b of the high pressure chamber 143 and into the inlet port 112 of the left ventricle 110.

When the liquid pressure of the left ventricle 110 is raised above the back pressure provided to the left atrium 120, the mitral valve 130 will close, and the pulse of liquid will flow through the aortic valve 114 from the left ventricle to the low pressure chamber 141. The volume of liquid that is pulsed through the aortic valve 114 will push an equal volume of liquid into the low pressure chamber 141. Once the low pressure 141 is filled, any excess liquid will flow into the open liquid tank 142, thereby preventing the back pressure applied to the left atrium 120 through the inlet port 122 from exceeding the desired maximum value (e.g., 90 mmHg).

When the gas pulse generator 144 ceases providing the gas pulse and permits the gas pressure in the outer chamber 145 to match that of the ambient environment, the pressure in the inner chamber 147 of the high pressure chamber 143 will drop below the level of pressure provided to the one-way valve 149b, because the highest point of the liquid in the compliant tube 148 is at a lower height than the liquid surface 142a of the open liquid tank 142, so the one-way valve 149b will open. When the one-way valve 149 opens, the pressure provided to the left ventricle 110 will start decreasing toward the pressure of the open liquid tank 142 (e.g., 30 mmHg). Once the liquid pressure in the left ventricle 110 has dropped below the back pressure provided to the left atrium 120 (e.g., 90 mmHg), the valve 130 will open.

When the mitral valve 130 opens, the pressure differential between the low pressure tank 141 (e.g., 90 mmHg) and the left ventricle 110 (e.g., below 90 mmHg and continuing to decrease) will cause the liquid in the low pressure tank to flow into the left atrium 120 and then through the mitral valve and into the left ventricle. As the liquid flows through the mitral valve 130 into the left ventricle 110, some liquid is displaced through the inlet port 112 and travels into the liquid outlet 143*b* of the high pressure chamber 143. The flow through the mitral valve 130 will continue until the pressure in the low pressure chamber 141 has decreased (due to the height of the liquid in the low pressure chamber decreasing) to equal the pressure in the open liquid tank 142, thereby equalizing the pressure in the left atrium 120 and the left ventricle 110 (e.g., 30 mmHg).

This completes one complete close and open cycle of the valve 130. For additional close and open cycles of the valve 130, the gas pulse generator 144 can provide additional gas pulses to the inner chamber 147 of the high pressure chamber 143, and the process described above will be repeated.

Once the apparatus 100 has achieved a steady state of alternating low pressure and high pressure pulses into the left atrium 120 and the left ventricle 110, respectively, a user may deploy a clip into the mitral valve or adjust an adjustable mitral valve, among other uses. By way of example, a user may insert the distal portion 14 of the repair device 10 (FIG. 2A) into either one of the introducers 116 or 126 for installation of a clip 55 (FIG. 10C) onto the mitral valve 130 to repair the posterior leaflet 132, for example, under simulated human cardiovascular conditions. In another example, a user may insert a device into either one of the introducers 116 or 126 for adjusting the internal circumference of the annular ring 134.

Although the apparatus 100 is shown in FIG. 11A as having inlet ports, outlet ports, introducers, and a gas purge valve, at particular locations, the apparatus need not have the configuration shown. The invention contemplates moving the inlet ports, the outlet ports, the introducers, and the gas purge valve to other locations along the same panels shown in FIG. 11A, or locations along other panels than those shown in the figures.

Furthermore, the orientation of the coaption line 135 of the mitral valve 130 relative to the panels of the left ventricle 110 and the left atrium 120 may be different than that shown in the figures, and the location of the papillary assemblies 150 may be different than that shown in the figures. However, it is preferred that the papillary assemblies be located on opposite sides of the left ventricle 110 from one another, and it is preferred that the coaption line 135 of the mitral valve 130 be oriented generally parallel to a line extending between the two papillary assemblies 150.

In the devices shown in the figures, particular structures are shown that are adapted to gather, secure, and repair heart valve leaflet tissue. The invention also contemplates the use of any alternative structures for such purposes, including structures having different lengths, shapes, and configurations. For example, although the capture tool is shown in the form of a grasping wire 22, the capture tool may take other forms, including for example, a pincer-like structure such as a clamp. Although the clamping member is shown in the form of a fork 30, the clamping member may have other configurations, such as an arm having a curved surface such that outer edges of the arm can serve as tines, a lattice structure, or any other structure capable of retaining leaflet tissue against the anvil 40 and the closed surface 41 of the outer shaft 16. The tissue support is shown as an anvil 40, but may take other forms, such as a corrugated surface, a set of pins extending from the closed surface 41 of the outer shaft 16, or any other shape that can guide leaflet tissue into a desired shape onto which a clip 55 can be attached.

In another example, although the catheter assembly 12 is described as being controllable by the movement of a particular configuration of buttons 61, 64, and 66 of a handle 60, any mechanisms that are adapted to control the movement and deployment of the containment tube, grasping wire, fork, and clip may be used. Furthermore, although the grasping wire 22 is shown as having a hook 24, the distal portion of the grasping wire may have any shape or configuration that may be adapted to grasp a target portion of valve leaflet tissue and help to capture such tissue inside or adjacent the outer tube such that a clip may be applied to the captured tissue.

Moreover, although the fork 30 is described as having two tines 31 that cooperate with the anvil 40 to capture leaflet tissue and form same into a W-shaped pleat, the invention contemplates forks having any number of tines cooperating with any number of anvils to form any number of pleats in the captured tissue. For example, a fork having a single tine may cooperate with two anvils that are laterally spaced apart from one another to form leaflet tissue into a pleat. It will be appreciated that the more pleats that are formed, the more the tissue of the valve leaflet can be tightened. In a particular embodiment, the tissue capture mechanism may include an outer tube 16 without an anvil portion extending from the inner surface 41 of the outer tube, wherein the tines 31 of the fork 30 are adapted to capture leaflet tissue in a single contiguous space defined within the outer tube 16, such that a portion of the inner surface of the outer tube may serve as an anvil portion. In such an embodiment without an anvil portion extending from the inner surface 41 of the outer tube 16, the hook 24 and the containment tube 20 may serve as an anvil portion to cooperate with the fork 30 to form leaflet tissue into a W-shaped pleat.

Although the fork 30 is described as including cam surfaces 34 and 35 for controlling lateral movement of the tines 31 as the fork is moved distally and proximally relative to the outer tube 16, other mechanisms may be used for controlling such lateral movement of the tines. For example, cam surfaces located at any location along the fork may slide against any portion of the outer tube 16 or any surface projecting therefrom to control lateral movement of the tines. Alternatively, a mechanism controlled by a dedicated button of the handle may be used to actuate lateral movement of the tines relative to the outer tube 16.

Although the device 10 is shown as being adapted to apply a single clip 55 onto a posterior leaflet 2, the invention contemplates devices that are adapted to apply a plurality of clips to the leaflet tissue during a single insertion of the device into a patient. For example, the gap 42 between the anvil portions 40*a* and 40*b* may be sufficiently large to accommodate a plurality of clips 55 in side-by-side relationship. In such an embodiment, while leaflet tissue is captured within the outer tube 16, the retaining arm 50 may be retracted to a first position to apply a first clip 55 to the tissue at a first target location, and the retaining arm may then be further retracted to a second position to apply a second clip 55 to the tissue at a second target location spaced from the first location.

Although the various delivery devices have been described herein in connection with tightening the posterior leaflet of a mitral valve, all of the delivery devices may be used on other heart valve leaflets, such as the anterior leaflet of the mitral valve (which is shown in FIG. 1 as the anterior leaflet 3), or on any other tissue of the body for which a reduction in the length of the tissue would be beneficial.

Although the invention herein has been described with reference to particular embodiments in which the catheter assembly is inserted into the patient via an introducer and through the apex of the heart (i.e., transapical insertion), it is to be understood that the invention contemplates embodiments in which the catheter assembly extends through a portion of the vasculature of the patient to reach the heart, for example, through a transfemoral or subclavian artery. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A simulation apparatus for mounting resected tissue, the apparatus comprising:
   a fixture having a first chamber, a second chamber, and an internal panel extending between the first and second chambers;
   a papillary assembly coupled to the fixture and having first and second spaced apart papillary attachment elements, each papillary attachment element being movable relative to the internal panel in at least one degree of freedom;
   a resected mitral valve attached to the internal panel and having a posterior leaflet, an anterior leaflet, and tendinae chordae, the tendinae chordae each attached at a first end to the posterior leaflet or the anterior leaflet and at a second end to one of the papillary attachment elements; and
   a pumping system configured to provide liquid flow through the resected mitral valve, the pumping system configured to alternatingly provide high pressure liquid pulses into the first chamber and a back pressure into the second chamber, the back pressure being less than the high pressure liquid pulses.

2. The apparatus as claimed in claim 1, wherein the pumping system is a partially-closed recirculating liquid flow system including a vertically-oriented low-pressure chamber, an open liquid tank having a substantially constant pressure, a high-pressure chamber comprising a compliant tube, and a gas pulse generator.

3. The apparatus as claimed in claim 1, wherein each papillary attachment element is movable relative to the internal panel in six degrees of freedom.

4. The apparatus as claimed in claim 1, wherein each papillary attachment element includes a suture plate, and wherein the tendinae chordae are each attached to the papillary attachment elements through a resected portion of a papillary muscle.

5. The apparatus as claimed in claim 1, wherein the fixture further includes first and second side panels disposed at opposite sides of the internal panel, and wherein the first and second papillary attachment elements each have a control rod extending through the respective first and second side panels.

6. The apparatus as claimed in claim 1, wherein the papillary attachment elements are each at least partially disposed inside the first chamber, and wherein a portion of the introducer is in fluid communication with the first chamber.

7. The apparatus as claimed in claim 1, wherein the papillary attachment elements are each at least partially disposed inside the first chamber, and wherein a portion of the introducer is in fluid communication with the second chamber.

8. The apparatus as claimed in claim 1, wherein the fixture includes an outlet port in fluid communication with the first chamber and the pumping system.

9. The apparatus as claimed in claim 8, wherein the outlet port includes an artificial aortic valve.

10. The apparatus as claimed in claim 8, wherein the outlet port is configured to open when a liquid pressure inside the first chamber exceeds a liquid pressure inside the second chamber, and the outlet port is configured to close when the liquid pressure inside the first chamber drops below the liquid pressure inside the second chamber.

11. A simulation apparatus for mounting resected tissue, the apparatus comprising:
    a fixture having a first chamber, a second chamber, and an internal panel extending between the first and second chambers, the fixture having at least one introducer configured to receive an elongated catheter assembly therethrough, the internal panel having an opening extending therethrough between the first and second chambers, the internal panel being configured to receive a resected mitral valve attached thereto and in fluid communication with the opening;
    a papillary assembly coupled to the fixture and having a papillary attachment element movable relative to the internal panel in at least one degree of freedom, the papillary attachment element configured to have tendinae chordae of the resected mitral valve attached thereto; and
    a pumping system configured to provide liquid flow through the resected mitral valve, the pumping system configured to alternatingly provide high pressure liquid pulses into the first chamber and a back pressure into the second chamber, the back pressure being less than the high pressure liquid pulses.

12. The apparatus as claimed in claim 11, wherein the papillary attachment element is movable relative to the internal panel in six degrees of freedom.

13. The apparatus as claimed in claim 11, wherein the papillary attachment element includes a suture plate configured to have the tendinae chordae of the resected mitral valve attached thereto through a resected portion of a papillary muscle.

14. The apparatus as claimed in claim 11, wherein the fixture further includes first and second side panels disposed at opposite sides of the internal panel, and wherein the papillary attachment element has a control rod extending through the first or second side panel.

15. A method of mounting resected tissue to a simulation apparatus, the method comprising:
    coupling a resected mitral valve to an internal panel extending between first and second chambers of a fixture, the resected mitral valve having a posterior leaflet, an anterior leaflet, and tendinae chordae each attached at a first end to the posterior leaflet or the anterior leaflet;

attaching a second end of each of the tendinae chordae to one of first and second spaced apart papillary attachment elements;

moving at least one of the first and second papillary attachment elements relative to the internal panel in at least one degree of freedom; and pumping liquid through the resected mitral valve by alternatingly providing high pressure liquid pulses into the first chamber and a back pressure into the second chamber, the back pressure being less than the high pressure liquid pulses, wherein during the pumping, the resected mitral valve alternatingly closes and opens in response to the alternating high pressure liquid pulses provided to the first chamber and back pressure provided to the second chamber, respectively.

16. The method as claimed in claim 15, further comprising inserting an elongated catheter assembly into at least one of the first and second chambers through an introducer, and during the pumping, using the elongated catheter assembly to install a clip onto at least one of the posterior and anterior leaflets of the resected mitral valve.

17. The method as claimed in claim 16, wherein the papillary attachment elements are each at least partially disposed inside the first chamber, and wherein the inserting step includes inserting the elongated catheter assembly into the first chamber through the introducer, such that the clip is delivered to the resected mitral valve through the first chamber.

18. The method as claimed in claim 16, wherein the papillary attachment elements are each at least partially disposed inside the first chamber, and wherein the inserting step includes inserting the elongated catheter assembly into the second chamber through the introducer, such that the clip is delivered to the resected mitral valve through the second chamber.

19. The method as claimed in claim 15, wherein the attaching step includes attaching each of the tendinae chordae to the papillary attachment elements through a resected portion of a papillary muscle.

20. The method as claimed in claim 15, wherein the moving step includes moving first and second control rods of the respective first and second papillary attachment elements, the first and second control rods extending through respective first and second side panels of the fixture disposed at opposite sides of the internal panel.

* * * * *